(12) United States Patent
Buscemi et al.

(10) Patent No.: US 11,505,658 B2
(45) Date of Patent: Nov. 22, 2022

(54) COATING COMPOSITION COMPRISED OF A HYDROPHILIC CROSSLINKER, A HYDROPHOBIC CROSSLINKER AND OPTIONALLY A HYDROGEL AND METHODS OF MAKING AND USING THE SAME

(71) Applicant: Harland Medical Systems, Inc., Eden Prairie, MN (US)

(72) Inventors: Paul Buscemi, Long Lake, MN (US); Gregory Carlson, Bloomington, MN (US)

(73) Assignee: Harland Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 17/570,912

(22) Filed: Jan. 7, 2022

(65) Prior Publication Data
US 2022/0127425 A1    Apr. 28, 2022

Related U.S. Application Data

(63) Continuation of application No. 16/490,752, filed as application No. PCT/US2018/020924 on Mar. 5, 2018, now Pat. No. 11,220,582.
(Continued)

(51) Int. Cl.
| C08J 3/24 | (2006.01) |
| A61L 29/08 | (2006.01) |
| A61L 29/14 | (2006.01) |
| C09D 5/14 | (2006.01) |
| C09D 139/06 | (2006.01) |

(Continued)

(52) U.S. Cl.
CPC ............ *C08J 3/245* (2013.01); *A61L 29/085* (2013.01); *A61L 29/145* (2013.01); *C08J 7/043* (2020.01); *C08J 7/056* (2020.01); *C09D 5/14* (2013.01); *C09D 139/06* (2013.01)

(58) Field of Classification Search
None
See application file for complete search history.

(56) References Cited

U.S. PATENT DOCUMENTS 3,408,429 A * 10/1968 Wichterle ........ B29D 11/00057
425/808
3,660,545 A * 5/1972 Wichterle ............... B29C 41/50
264/2.6

(Continued)

FOREIGN PATENT DOCUMENTS

EP  1852138  11/2007
EP  2213325   8/2010
(Continued)

OTHER PUBLICATIONS

Irgacure 819 TDS (Year: 2001).*
(Continued)

*Primary Examiner* — Peter A Salamon
(74) *Attorney, Agent, or Firm* — Fish & Richardson P.C.

(57) ABSTRACT

The present invention relates to coatings for devices such as medical devices that are useful for coating a variety of different types of material surfaces, including polymer and metal surfaces. The present invention also includes the method of using the coated device and methods to make the coated device and coating.

20 Claims, 1 Drawing Sheet

Related U.S. Application Data

(60) Provisional application No. 62/466,541, filed on Mar. 3, 2017.

(51) Int. Cl.
*C08J 7/043* (2020.01)
*C08J 7/056* (2020.01)

(56) References Cited

U.S. PATENT DOCUMENTS

| | | | | |
|---|---|---|---|---|
| 4,053,317 | A * | 10/1977 | Naka | G03F 7/027 |
| | | | | 430/908 |
| 4,113,224 | A * | 9/1978 | Clark | B29C 37/005 |
| | | | | 249/105 |
| 4,197,266 | A * | 4/1980 | Clark | B29C 35/0894 |
| | | | | 264/2.3 |
| 4,330,612 | A * | 5/1982 | Tashiro | G03F 7/033 |
| | | | | 430/196 |
| 4,338,879 | A | 7/1982 | Makeev et al. | |
| 4,436,764 | A | 3/1984 | Nakazima et al. | |
| 4,661,573 | A * | 4/1987 | Ratkowski | C08F 230/08 |
| | | | | 351/159.01 |
| 4,983,716 | A * | 1/1991 | Rao | C08L 67/08 |
| | | | | 525/445 |
| 5,201,724 | A * | 4/1993 | Hukins | A61M 25/0045 |
| | | | | 604/540 |
| 5,262,033 | A | 11/1993 | Zega et al. | |
| 5,429,618 | A | 7/1995 | Keogh | |
| 5,443,453 | A | 8/1995 | Walker et al. | |
| 5,454,650 | A | 10/1995 | Yamaguchi | |
| 5,531,715 | A | 7/1996 | Engelson et al. | |
| 5,538,512 | A | 7/1996 | Zenzon et al. | |
| 5,541,167 | A | 7/1996 | Hsu et al. | |
| 5,603,991 | A | 2/1997 | Kupiecki et al. | |
| 5,688,855 | A * | 11/1997 | Stoy | C09D 175/04 |
| | | | | 524/378 |
| 5,702,823 | A | 12/1997 | Forrestal et al. | |
| 6,020,445 | A * | 2/2000 | Vanderlaan | C08F 230/08 |
| | | | | 526/279 |
| 6,254,921 | B1 | 7/2001 | Chappa et al. | |
| 7,381,273 | B2 | 6/2008 | Collins | |
| 7,597,937 | B2 | 10/2009 | Anderson et al. | |
| 8,105,259 | B2 * | 1/2012 | Michishita | A61M 25/007 |
| | | | | 604/4.01 |
| 8,133,545 | B2 | 3/2012 | Anderson et al. | |
| 8,245,660 | B2 | 8/2012 | Dillon et al. | |
| 8,247,019 | B2 | 8/2012 | Anderson et al. | |
| 8,691,342 | B2 * | 4/2014 | Soucek | C08G 59/1488 |
| | | | | 427/384 |
| 9,193,886 | B2 * | 11/2015 | Soucek | C09D 133/16 |
| 10,875,048 | B2 | 12/2020 | Surma et al. | |
| 11,220,582 | B2 | 1/2022 | Buscemi et al. | |
| 2001/0040096 | A1 | 11/2001 | Yamamoto et al. | |
| 2005/0271778 | A1 * | 12/2005 | Petereit | A61K 9/2893 |
| | | | | 426/302 |
| 2006/0210699 | A1 | 9/2006 | Collins | |
| 2007/0043160 | A1 * | 2/2007 | Hanley | A61L 31/10 |
| | | | | 524/502 |
| 2007/0224236 | A1 * | 9/2007 | Boden | A61L 27/34 |
| | | | | 424/423 |
| 2007/0269480 | A1 * | 11/2007 | Richard | A61L 29/16 |
| | | | | 514/1.3 |
| 2009/0223682 | A1 | 9/2009 | Ramos | |
| 2009/0287135 | A1 | 11/2009 | Michishita et al. | |
| 2010/0106103 | A1 * | 4/2010 | Ziebol | A61M 25/0105 |
| | | | | 604/265 |
| 2010/0129545 | A1 | 5/2010 | Buck et al. | |
| 2010/0280146 | A1 * | 11/2010 | Vanderlaan | A61L 27/26 |
| | | | | 264/2.6 |
| 2011/0014386 | A1 | 1/2011 | Dillon | |
| 2011/0250442 | A1 | 10/2011 | Castro et al. | |
| 2012/0058355 | A1 * | 3/2012 | Lee | C09D 101/286 |
| | | | | 427/407.1 |
| 2012/0201965 | A1 * | 8/2012 | Soucek | C08F 220/14 |
| | | | | 524/508 |
| 2013/0197454 | A1 * | 8/2013 | Shibata | A61M 25/0045 |
| | | | | 604/264 |
| 2013/0341811 | A1 * | 12/2013 | Alli | G02B 1/04 |
| | | | | 264/1.38 |
| 2014/0239239 | A1 * | 8/2014 | Cha | H01M 4/134 |
| | | | | 525/218 |
| 2014/0275460 | A1 * | 9/2014 | Tamareselvy | C08F 226/06 |
| | | | | 526/264 |
| 2014/0302327 | A1 * | 10/2014 | Soucek | C08F 220/14 |
| | | | | 428/414 |
| 2015/0040825 | A1 | 2/2015 | Kulakovsky | |
| 2015/0329604 | A1 * | 11/2015 | Parker | C07K 14/435 |
| | | | | 428/221 |
| 2015/0360459 | A1 * | 12/2015 | Desmet | B41C 1/10 |
| | | | | 101/463.1 |
| 2017/0015850 | A1 * | 1/2017 | Yoshino | C09D 11/107 |
| 2017/0058135 | A1 * | 3/2017 | Kohzuki | C09D 11/101 |
| 2017/0058423 | A1 | 3/2017 | Mine et al. | |
| 2019/0070630 | A1 | 3/2019 | Surma et al. | |
| 2020/0002565 | A1 * | 1/2020 | Buscemi | C09D 139/06 |

FOREIGN PATENT DOCUMENTS

| | | |
|---|---|---|
| EP | 2371402 | 10/2011 |
| EP | 2810680 | 12/2014 |
| EP | 3505344 | 7/2019 |
| GB | 1496345 | 12/1977 |
| JP | 2003-171579 | 6/2003 |
| JP | 2008-214385 | 9/2008 |
| WO | WO 89/05671 | 6/1989 |
| WO | WO2007/109332 | 9/2007 |
| WO | WO2007/109333 | 9/2007 |
| WO | WO 2012/027678 | 3/2012 |
| WO | WO2018/161079 | 9/2018 |
| WO | WO2019/050962 | 3/2019 |

OTHER PUBLICATIONS

Database WPI, Week 199735, Thomson Scientific, Jun. 24, 1997, 3 pages. Abstract.

Database WPI, Week 201612, Thomson Scientific, Jan. 21, 2016, 3 pages. Abstract.

"RDX-XL Series Coating Systems," Harland Medical Systems, Inc., 2009, 4 pages.

* cited by examiner

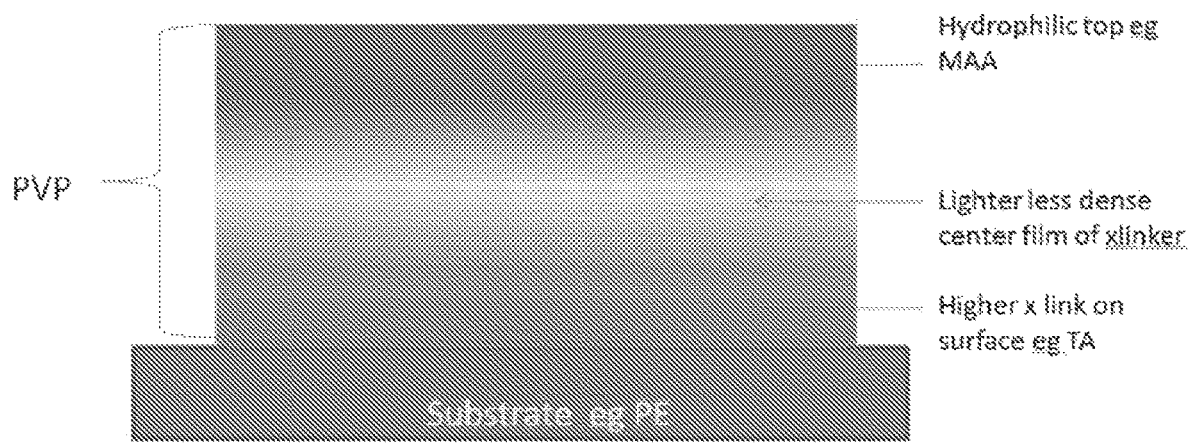

COATING COMPOSITION COMPRISED OF A HYDROPHILIC CROSSLINKER, A HYDROPHOBIC CROSSLINKER AND OPTIONALLY A HYDROGEL AND METHODS OF MAKING AND USING THE SAME

CROSS REFERENCE TO RELATED APPLICATIONS

This application is a continuation of U.S. patent application Ser. No. 16/490,752, filed Sep. 3, 2019, which is a national stage application under 35 U.S.C. § 371 and claims the benefit of PCT Application No. PCT/US2018/020924 having an international filing date of Mar. 5, 2018, which designated the United States, which PCT application claimed the benefit of priority under 35 U.S.C. § 119(e) to U.S. Provisional Patent Application Ser. No. 62/466,541, filed on Mar. 3, 2017. The entire disclosures of U.S. patent application Ser. No. 16/490,752, PCT Application No. PCT/US2018/020924 and U.S. Provisional Patent Application No. 62/466,541 are incorporated herein by reference.

FIELD OF THE INVENTION

The present invention relates to coatings for devices, the method of making the coating, the method of coating a device, and the method of using a device with a coating.

BACKGROUND

Many coatings for polymers and metals are described in the literature. Most are specific for a metal or a polymer, but not both. When more than one material is used for a device, separate solutions are required to bond coatings to the different materials. Similarly, multiple solutions can be needed if more than one polymer is used in a device as the different polymers, similar to other materials like metal, can have differing hydrophilicity. Many require surface activation in order to bond the coating to the surface of a substrate. Furthermore, known coating processes require multiple coating processes to coat a device.

SUMMARY

An aspect of the present invention is directed to a coating composition that includes hydrophobic/hydrophilic or polar gradient in a coating such that the coating includes a hydrophilic crosslinker (as compared to the hydrophobic carrier in the coating) and a hydrophobic crosslinker, which are at least partially miscible. In some embodiments, the coating can also include a polymer or hydrogel. Other aspects of the invention include methods of making the coating, methods of using the coating, and devices containing the coating.

The hydrophilic and hydrophobic crosslinkers or chain extending molecules are reactive molecules that can adhere to surfaces and crosslink and extend high molecular weight polymer coatings. Advantageously, the coating can be used on different surfaces. At least one crosslinking material can be, for example a triacrylate or other similar molecules, compounds containing these molecules, and combinations thereof. The crosslinking materials can be used to obtain a differential distribution of the crosslinker in the coating. Other examples of crosslinking materials can include vinyl siloxane, vinyl pyrrolidone, methacrylic acid, hydroxyethyl methacrylate, a diacrylate, a di- or tri vinyl functional compound, a methyl-propyl, benzyl compounds with vinyl functional groups, and combinations thereof. These hydrophilic and hydrophobic reactive molecules can be miscible to some extent, acting as cross-linkers and chain extenders for polymeric coatings. The crosslinked polymer can entrap a polymer. The polymer can be a hydrogel. The polymer can be polyvinylpyrrolidone (PVP). Other polymers can include a polyvinyl alcohol, a polyacrylate, an agarose, a methylcellulose, hyaluronic acid, polyisocyanates, a urethane coating, a water miscible epoxide, an alginate, or combinations of two or more of these polymers. The crosslinkers can be induced to crosslink and form the crosslinked polymer by free radical, ionic or other mechanisms.

The composition of the surface to be coated with the composition of the present invention, for example, a medical device, can determine which of the cross-linkers (i.e., hydrophilic or hydrophobic crosslinkers) will be preferentially adsorbed to the surface. This surface composition can make the first reaction between the surface and the adsorbed crosslinker preferential or proceed at a more efficient or higher rate than the other crosslinker(s). When a second crosslinker is used in the coating, the second crosslinker can align in the coating according to the polarity or hydrophobic/hydrophilic characteristics. Combinations of different crosslinkers and the substrate can be adjusted to optimize the bonding, thickness or lubricity of the final product.

In some embodiments, the coating can have a variable concentration of components that are hydrophilic nature, which can be determined by the thickness of the coating or the concentration of the coating solution. The thickness of the coating can be controlled by the crosslinking components, which can be acrylates in some embodiments. The thickness can also be controlled by the extraction rate of the coating solution to the substrate.

The crosslinking component can entrap the polymer, for example PVP. The stratification of crosslinking components in the coating can result in a variable hydrophilic nature of the coating, can provide higher strength of the coating near the substrate, and control the hydrogel water absorption near the surface.

The present invention has advantages over the prior art and addresses the need for separate solutions to bond to metals and polymers of differing polarity, hydrophilicity and hydrophobicity. The use of coatings that contains gradients of hydrophobic and hydrophilic crosslinkers/compounds allows for a single coating process, regardless of the material of the substrate to be coated. Advantageously, the use of these different compounds also allows for multiple compounds to be bonded or attached to the coating.

An aspect of the invention is a coated substrate. The coated substrate includes a substrate that has a polar characteristic at an exterior surface. The coated substrate also has a gradient coating which includes at least one crosslinker. The coating has a variable concentration of the crosslinker between an substrate surface and an outer surface of the gradient coating. The substrate surface of the gradient coating is adjacent to the exterior surface of the substrate. The substrate surface of the gradient coating has a first coating polar characteristic and the outer surface of the gradient coating comprises a second coating polar characteristic.

An aspect of the invention is a method to coat a substrate. The method includes mixing at least one crosslinker, at least one polymer, and an initiator to produce a pre-coating mixture. The mixture is applied to the substrate. A reaction of the crosslinker is initiated to produce the a gradient crosslinked coating on the substrate. The crosslinked coating entraps the polymer. The coating has a variable concentration of the crosslinker between an substrate surface of the coating and an outer surface of the coating. The substrate surface of the coating is adjacent to the exterior surface of the substrate. The substrate surface of the coating comprises a first coating polar characteristic and the outer surface of the coating comprises a second coating polar characteristic.

An aspect of the invention is a gradient coating. The coating includes at least one crosslinker, and a high molecular weight polymer.

An aspect of the invention is a method to produce a pre-coating. The method includes mixing at least one crosslinker, a high molecular weight polymer, and an initiator to produce a pre-coating. A ratio of the crosslinker, the high molecular weight polymer and the initiator is between about 1:0.1:0.005 and about 0.02:1.0:0.02.

An aspect of the invention is a pre-coating material for use on a medical device. The material includes a crosslinker, an initiator, and a high molecular weight polymer. The ratio of the crosslinker, the high molecular weight polymer, and the initiator is between about 1:0.1:0.005 and about 0.02:1.0:0.02.

BRIEF DESCRIPTION OF THE FIGURES

FIG. 1 illustrates an embodiment of the present invention utilizing two crosslinkers or network former to form the crosslinked polymer, and a high molecular weight polymer.

DETAILED DESCRIPTION

An aspect of the invention is a coated substrate. The substrate includes a polar characteristic on its exterior surface. The coating includes at least one crosslinker. The crosslinker includes a variable concentration between an substrate surface of the coating and an outer surface of the coating. The substrate surface of the coating has a first coating polar characteristic and the outer surface of the coating has a second coating polar characteristic. The substrate surface of the coating is adjacent or in contact with the surface of the exterior surface of the substrate.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material. The variation can be a result of variable concentrations of the crosslinker in the coating. FIG. 1 illustrates an embodiment of the present invention utilizing two crosslinkers and PVP as the polymer.

The term crosslinker is used throughout the description of the invention to include both monomers that crosslink to form a crosslinked polymer and network formers, which are long chain compounds that can intertwine with itself, for example methacrylic acid.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

The ratio of the high molecular weight polymer to the crosslinker ranges from about 1:0.05 to about 1:1 for all formulations regardless of the number of components. The ratio of the high molecular weight polymer to the initiator is between about 1:0.001 and about 1:01. In some embodiments, the ratio of a first crosslinker of the second crosslinker is between about 1:0.1 and about 1:1. In some embodiments, the ratio of a crosslinker, a high molecular weight polymer and the initiator is between about 1:0.1: 0.005 and about 0.02:1.0:0.02.

An aspect of the invention is a method to coat a substrate. The method includes mixing at least one crosslinker, at least one polymer, and an initiator to produce a pre-coating mixture. The pre-coating mixture is applied to a substrate. Then a reaction is initiated to crosslink the crosslinker(s) in the pre-coating mixture to produce a gradient crosslinked coating on the substrate. The crosslinked coating entraps the polymer, and the gradient coating includes a variable concentration of the crosslinker between an substrate surface of the coating and an outer surface of the coating such that the substrate surface of the gradient coating comprises a first coating polar characteristic and the outer surface of the coating comprises a second coating polar characteristic. The substrate surface of the coating is adjacent to the exterior surface of the substrate.

The thickness can be controlled by the concentration of the coating solution in the solvent, by the extraction rate used during application of the coating, the amount of polymer in the coating solution, or a combination of these methods to control the thickness. The thickness of the coating on the substrate can be between about 0.5 microns and about 10 microns. For a thicker coating, a higher concentration of the coating solution in the solvent can be used. The higher concentration can be between about 5 wt. % and about 15 wt. % of the coating solution in the solvent. For thicker coatings, the substrate can be withdrawn from the coating solution at a faster rate compared to the rate used for a thinner coating. In some embodiments, the extraction rate for a thick coating (i.e. between about 0.5 microns and about 10 microns) can be at a rate of between 0.5 cm/s and 1 cm/s. In some embodiments, the extraction rate in general can be between about 0.2 cm/s and 1 cm/s.

The pre-coating mixture can be applied using any suitable means. The pre-coating mixture can be applied to the substrate by dipping, spraying, painting, submerging, or other methods. The pre-coating mixture can be applied uniformly on the substrate or can vary on the substrate.

The pre-coating mixture includes at least one solvent. The solvent can be any suitable alcohol, including isopropanol, polypropanol, propanol, ethanol, methanol, dimethyl sulfoxide (DMSO), water and combinations of. The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, SEBs, and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings.

In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

The ratio of the high molecular weight polymer to the crosslinker ranges from about 1:0.05 to about 1:1 for all formulations regardless of the number of components. The ratio of the high molecular weight polymer to the initiator is between about 1:0.001 and about 1:01. In some embodiments, the ratio of a first crosslinker of the second crosslinker is between about 1:0.1 and about 1:1. In some embodiments, the ratio of a crosslinker, a high molecular weight polymer and the initiator is between about 1:0.1:0.005 and about 0.02:1.0:0.02.

An aspect of the invention is a method to produce a pre-coating for use with the invention. The method includes providing at least one crosslinker, a high molecular weight polymer, and an initiator. Advantageously, the method to produce the pre-coating does not require the reaction to take place in a special room or contained area to protect the molecules against premature reaction with visible light. Rather, since the present invention utilizes initiators that operate over the ultraviolet spectrum, the materials do not require special handling during mixture to produce the precoating.

The ratio of the crosslinking material to the polymer to the initiator can be between about 1:0.05 and 1:1. In some embodiments, the pre-material can be provided with an excess of initiator to drive the crosslinking reaction to completion. The ratio of the high molecular weight polymer to the crosslinker ranges from about 1:0.05 to about 1:1 for all formulations regardless of the number of components. The ratio of the high molecular weight polymer to the initiator is between about 1:0.001 and about 1:01. In some embodiments, the ratio of a first crosslinker of the second crosslinker is between about 1:0.1 and about 1:1. In some embodiments, the ratio of a crosslinker, a high molecular weight polymer and the initiator is between about 1:0.1:0.005 and about 0.02:1.0:0.02.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

An aspect of the invention is a pre-coating material for use on a medical device. The coating includes at least one crosslinker, and a polymer. An initiator is used to crosslink a crosslinking agent, but the initiator is not attached to the crosslinker. The coating provides a gradient concentration of the crosslinker when applied to a substrate.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

An aspect of the invention is a coating for use on a medical device. The coating includes at least one network former or one crosslinked polymer, and a high molecular weight polymer, and less than about 0.01 wt. % of incidental materials. The coating provides a gradient density when applied to a substrate. The gradient is generated primarily by the network former or crosslinking components.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between about 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

An aspect of the invention is a pre-coating material for use on a medical device. The coating includes at least two crosslinkers, and at least one polymer. An initiator is used to crosslink the crosslinkers and entrap the polymer, but the initiator is not attached to the crosslinker. The crosslinked coating provides a gradient concentration when applied to a substrate.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the stratification of the components based on the components polarity or hydrophobic/hydrophilic nature at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

An aspect of the invention is a coating for use on a medical device. The coating includes a crosslinked polymer, and at least one polymer. The coating provides a polar gradient when applied to a substrate.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinylchlorides, styrene ethylene butadienes (SEBs), and combinations thereof. In some embodiments, the polar characteristic of the exterior surface of the substrate can be altered to assist in bonding of the coating, or to alter the alignment of the polarity or hydrophobic/hydrophilic nature of the coating at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

An aspect of the invention is a gradient coating. The coating includes a crosslinked polymer and a high molecular weight polymer, wherein the gradient in the gradient coating is based on density of the crosslinker of the crosslinked polymer.

The substrate can be contact lenses, catheters (including cardiovascular catheters and urological catheters), wires (including guidewires), springs, leads (for example a pacemaker lead), stents, implants, antennas, sensors, tubing, syringes, catheters, i.v. bag needles, needles, ventricular assist device components, and trochars, or combinations of two or more of these devices. The material of the substrate can be a polymer, a metal, a glass, polyester block amides (for example Pebax™, a silicone rubber, nylons, polyvinyl-chlorides, styrene ethylene butadienes (SEBs), and combinations thereof. In some embodiments, the polar characteristic of the exterior surface of the substrate can be altered to assist in bonding of the coating, or to alter the alignment of the polarity or hydrophobic/hydrophilic nature of the coating at the surface between the coating and the substrate or on the exterior or outer surface of the coating. By way of example, the polar characteristic of the exterior surface of a substrate can be altered from hydrophobic to less hydrophobic as compared to its initial polar characteristic, or from hydrophilic to less hydrophilic as compared to its initial polar characteristic. When more than one material is used in a medical device, the polar characteristic of the substrate can be different at different locations corresponding to the different materials. The medical device can be used in contact with blood, plasma, and the like.

The polar characteristic of the substrate can result in the substrate being hydrophobic or hydrophilic. The polar characteristic can vary through the coating, such that the coating is hydrophobic at an substrate surface of the coating, gradually increasing in hydrophilic properties to the exterior surface which is more hydrophilic, or at least less hydrophobic, compared to the characteristic at the substrate surface of the coating. Alternatively, the polar characteristic can vary through the coating, such that the coating is hydrophilic at an substrate surface of the coating, then gradually decreases in hydrophilic properties, such that the exterior surface is hydrophobic, or at least less hydrophilic, compared to the characteristic at the substrate surface of the coating. If more than one crosslinking material is utilized, the additional crosslinker can also vary in a similar manner as the first crosslinking material. For example, if a first crosslinker is more hydrophilic than a second crosslinker, and a substrate is hydrophilic, the crosslinking components can align such that the first crosslinker is adjacent to the surface of the substrate and second crosslinker in the coating is closer to the outer surface of the coating. If additional crosslinkers are used in the coating, the variation and alignment of the additional crosslinkers can be located in the coating based on the polarity and hydrophobic/hydrophilic nature compared to other crosslinking materials in the coating. In some embodiments when more than one crosslinker is utilized, the different crosslinkers can not only crosslink with other similar crosslinkers, but can also crosslink with different crosslinkers, which can result in additional polarities of the crosslinked material within the overall crosslinked material.

In some embodiments, for example where only one crosslinker is utilized in the coating, layering of the coating can be achieved based on the density variations in the coatings. In some embodiments, the coating can be more dense at an substrate surface where the coating bonds or associates to a surface of the substrate and less dense on the exterior surface of the coating. In other embodiments, the coating can be less dense at an substrate surface compared to the density of the coating at an outer surface.

The polar characteristic of the coating can allow for the coating and the substrate to create a bond. Thus, an advantage of the present invention is that the coating adheres to the substrate. The strength of the bond between the substrate and the coating can be between about 1 gm and about 500 gm. In some embodiments, when the entire substrate includes the coating, then the coating can bond to itself forming a sleeve around the substrate. The sleeve embodiment can be useful where the substrate is not likely to bond to the coating, but can also provide additional strength between the coating and the substrate even when the coating and the substrate create a bond.

The coating can be tailored for particular applications. For example, if an application requires that the bond between the substrate and the coating is strong, then the coating can be tailored so that it bonds with the substrate. For example, if the substrate is a polymer and the exterior surface of the polymer substrate is hydrophobic, then the coating can be formed such that the coating exhibits a gradient where the hydrophobic crosslinker is close to the substrate and more hydrophilic crosslinkers are located at the surface. Embodiments of the invention can result in the middle of the film providing additional strength to the coating by mono-functional network formers that have intermediate concentration of the crosslinker that is designed to adsorb to the surface of the substrate and that of the crosslinker or network former selected to reside on the film surface. The vinyl polyethylene and polypropylene oxides are such compounds which can be used as a crosslinker. Other embodiments can increase the water content of the coating by addition of hydroxylated compounds as methacrylic acid (MAA), which can be used as a crosslinker. More than one of these embodiments can be combined to tailor the coating for a particular application. Furthermore, it is possible to produce more than one layer or more than one coating layers such that there are multiple layers in the coating created by using the same or different coating materials on the substrate. In some embodiments, the coating can comprise between about one and about five layers, where each layer can be the same or different. The coating can be on a portion of the first surface of the substrate such that between about 1% and about 99% of the first surface is coated with the coating. The coating can be on a portion of one or more surfaces of the substrate such that between about 1% and about 99% of at least one surface of the substrate can be coated. In some embodiments, the coating can be on the entire first surface or on more than one surface of the substrate such that it covers each surface of the substrate.

The gradient can be modulated by the choice of solvent used with the coating, the drying time (evaporation rate), temperature, and its polarity. By decreasing the polarity with a less polar solvent, a less polar crosslinker or network former can disperse into the coating. A more polar solvent can force a less polar crosslinker to the surface of the coating. The solvent can be any suitable alcohol, including isopropanol, polypropanol, propanol, ethanol, methanol, dimethyl sulfoxide (DMSO), water and combinations of. The drying time can be between about 2 minutes and about 10 minutes, in some embodiments between about 4 minutes and about 5 minutes. The drying temperature can be between about 20° C. and about 50° C., in some embodiments between about 27° C. and about 40° C., in some embodiments about 35° C. The drying time can depend on the coating thickness and solvent vapor pressure.

At least one crosslinker or network former can be used to create the crosslinked polymer, or the networked polymer. The crosslinker can be a vinyl compound (including polyvinyl ethylene glycol, polyvinyl siloxane, vinyl pyrrolidone, vinyl silanes, vinyl polyethylene oxide, and vinyl polypropylene oxide), ethyleneglycol dimethacrylate, an acrylate compound (for example MAA), an epoxy compound, a urethane compound, an isocyanate compounds, triacrylate (for example, trimethylolpropane triacrylate), methacrylate, methacrylic acid, and hydroxyethyl methacrylate, and combinations or two or more of these crosslinkers. The crosslinker can be activated by free radical or ionic mechanisms or by dehydration to produce the crosslinked polymer with an initiator. The initiator can be a photo or radioactive initiator, for example a UV initiator. The wavelength to react the initiator will depend upon the initiator properties. Initiators useful for the present invention preferably do not react with visible light typically found in a room or a lab as such an initiator would require additional equipment in order to prevent the reaction from occurring prematurely. Rather, in some embodiments, the initiator can react at a wavelength less than about 280 nm and a luminance between about 3 to about 5 mW/cm$^3$. Advantageously, the initiator does not need to be attached to the crosslinker prior to reacting the crosslinker. Rather, when the initiator is used, it can simply be added to the reaction. Furthermore, the initiator becomes active without heat. Suitable photo initiators include 1-hydroxy-cyclohexyl-phenyl-ketone (for example Ciba® IRGACURE® 184), or 13-4-(2-Hydroxyethoxy)-phenyl8-2-hydroxy-2-methyl-1-propane-1-one (for example Ciba® IRGACURE® 2959), 2-Hydroxy-4'-(2-hydroxyethoxy)-2-methylpropiophenone, or combinations thereof.

The crosslinkers or network formers serve at least two purposes relevant to the invention. First, the crosslinkers can be used to bond the coating to a surface of the substrate. Second, the crosslinker can be used to entrap the hydrating polymer and/or an additive. Combinations of more than one crosslinkers can be utilized for a particular application. For example, a first crosslinker can be chosen based on its polarity to provide good adhesion to a surface of a substrate. A second crosslinker can be selected to provide lubricity to the coating and to increase the strength of entanglement of the high molecular weight hydrating polymer.

A high molecular weight polymer can be entrapped in the crosslinked polymer. Suitable high molecular weight polymers will have an average molecular weight above about 30,000. The average molecular weight of the high molecular weight polymers can be between about 30,000 and about 1.5M. Low molecular weight polymers would not be suitable for the invention because they would not entrap within the crosslinked polymer. Suitable high molecular weight polymers include polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, and the like, and combinations of two or more of these high molecular weight polymers.

The concentration of each crosslinker components in the coating can be between about 0.01 wt. % and 0.5 wt. % of the total mass of the coating. When more than one crosslinker is utilized, then the total concentration of all crosslinker components is between about 0.02 wt. % and about 2 wt. % of the total mass of the coating. In some embodiments where more than one crosslinker is utilized, the coating can include between 0.01 wt. % and about 2 wt. % of a crosslinker or chain extending compound, and between about 0.01 wt. % and about 2.0 wt. % of each additional crosslinking or chain extending compound. The ratio of the first crosslinker to a second crosslinker can be between about 1:0.1 and about 1:1. The concentration of the high molecular weight polymer in the coating can be between about 3 wt. % and about 15 wt. % of the coating. The concentration of the coating solution in a solvent can be between about 3 wt. % and about 15 wt. %. The solvent can be present in the coating in an amount between about 85 wt. % and about 97 wt. %. Additives can be present in the coating in an amount between 0.05 wt. % and 0.1 wt. %. Other incidental materials (for example unreacted components) can be present in the coating in an amount less than about 0.1 wt. % of the total weight percent of the coating.

The thickness of the coating on the substrate can be between about 0.5 microns and about 10 microns. The use of the substrate can dictate the thickness of the coating. A thickness of between about 0.5 microns and about 10 micron can provide if the coating requires a longer dry-out time.

In some embodiments of the invention, additives can be incorporated into the coating. Suitable additives include antimicrobial (including antibacterial) agents, binders, rheology modifiers, or colorants, and combinations of two or more additives. Suitable antimicrobial agents can include a silver compound, chlorhexidine, ciprofloxacin, and combinations thereof. Suitable rheology modifiers can include pluronics, alginates, carboxymethyl cellulose and combinations thereof. Suitable colorants can include dyes or oxide pigments, and combinations thereof. The total concentration of the additives in the coating can be between about 0.05 wt. % and about 0.1 wt. % of the total weight of the coating, with each additive used contributing to a portion of this total weight.

EXAMPLES

Example 1

This example illustrates the preparation of two coating compositions in accordance with the present invention.

Coating compositions A and B were prepared by combining the ingredients in the relative amounts by mass shown in Table 1.

TABLE 1

| Component | Composition A | Composition B | Composition C |
|---|---|---|---|
| Polyvinylpyrrolidone (PVP) | 1.0 | 3.0 | 1.0 |
| Trimethylolpropane triacrylate (TMPTA) | 0.15 | 0.025 | 0.15 |
| Methacrylic acid (MAA) | — | 0.15 | 0.05 |
| Ethyleneglycol dimethacrylate (EGDMA) | — | 0.025 | — |
| Irgacure 184 | 0.0075 | — | 0.1 |
| Irgacure 2959 | — | 0.01 | — |

Isopropyl alcohol was added as a solvent in an amount of 5 weight percent of the composition.

Example 2

This example illustrates the production of a catheter coated with Composition A. A urological catheter made of polyethylene was coated with Composition A and then subjected to UV radiation with a wavelength below 280 nm and luminance of 3 to 5 mW/cm$^2$ to initiate crosslinking. The resulting coated catheter has a coating that is well bonded to the catheter and has a high water content and a long dry out time.

Example 3

This example illustrates the production of a catheter coated with Composition B. A urological catheter made of polyethylene was coated with Composition B and then subjected to UV radiation with a wavelength below 280 nm and luminance of 3 to 5 mW/cm$^2$ to initiate crosslinking. The resulting coated catheter has a coating that is well bonded to the catheter and has a high water content and a long dry out time.

Example 4

This example illustrates the production of a catheter coated with Composition C. The total concentration of the coating solution ranges between about 3% and about 7%. A urological catheter made of polyvinylchloride was coated with Composition A and then subjected to UV radiation with a wavelength below 280 nm and luminance of 3 to 5 mW/cm$^2$ to initiate crosslinking. The resulting coated catheter has a coating that is well bonded to the catheter and has a high water content and a long dry out time.

Example 5

This example illustrates the average frictional force of the coating for fifty cycles (unless noted) for different compositions. Table 2 provides the average frictional force for these compositions. The nomenclature of the different compositions is as follows: First number corresponds with a solvent—5 is IPA, and 6 is methanol; the second number corresponds with the composition of the coating—1 is Composition A, 2 is Composition B; the third number indicates whether a low amount of a crosslinker was used which is indicated by the number 0, while a high amount of the crosslinker is indicated with 6; the letter indicates a test sample. This data therefore accounts for different solvents used in the coatings, and whether there is a low total amount of a crosslinker (about 0.05 wt. %) or combination of crosslinkers compared to a higher amount of a crosslinker (about 2 weight %) in the coating.

TABLE 2

| Sample | Average Frictional Force (gm) |
|---|---|
| 510a | 9.17 |
| 510b | 10.48 |
| 510c | 8.95 (15 cycles) |
| 510d | 29.4 |
| 526e | 20.19 |
| 526e | 15.08 |
| 526f | 29.71 |
| 616a | 14.89 |
| 616b | 21.66 |
| 626c | 17.06 |
| 626d | 20.27 |
| 626e | 9.83 |
| 626f | 20.01 |

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A polymerizable coating composition, comprising:
   an initiator;
   a crosslinker configured to form a crosslinked polymer;
   a high molecular weight component, wherein the high molecular weight component has an average molecular weight between about 30,000 and 1.5M; and
   a solvent;
   wherein polymerization of the composition on a substrate yields a coating comprising the high molecular weight component entrapped in the crosslinked polymer;
   wherein the polymerizable coating composition is configured to bond to the substrate, thereby forming a coating on the substrate, wherein the formed coating comprises a polar characteristic, and wherein the polar characteristic varies through the coating, such that the coating is hydrophobic at a substrate surface of the coating, gradually increasing in hydrophilic properties to an exterior surface of the coating which is more hydrophilic compared to the substrate surface of the coating.

2. The coating composition of claim 1, wherein the crosslinker comprises about 0.01 wt % to about 0.5 wt % of the polymerizable coating composition.

3. The coating composition of claim 1, wherein the high molecular weight component comprises about 3 wt % to about 15 wt % of the polymerizable coating composition.

4. The coating composition of claim 1, wherein the solvent comprises about 85 wt % to about 97 wt % of the polymerizable coating composition.

5. The coating composition of claim 1, wherein a ratio of the crosslinker, the high molecular weight component, and the initiator is between about 1:0.1:0.005 and about 0.02:1.0:0.02.

6. The coating composition of claim 5, wherein the ratio is about 1:0.15:0.0075.

7. The coating composition of claim 1, wherein the initiator is a photo reactive initiator.

8. The coating composition of claim 1, wherein the initiator reacts at a wavelength less than about 280 nm and a minimal luminance between about 3 to about 5 mW/cm$^2$.

9. The coating composition of claim 1, further comprising an additional crosslinker.

10. The coating composition of claim 9, wherein the crosslinker and the additional crosslinker stratify in the coating such that the first crosslinker arranges in a first layer and the second crosslinker arranges in a second layer.

11. The coating composition of claim 1, wherein the crosslinker comprises a polyvinyl ethylene glycol, a polyvinyl siloxane, a vinyl pyrrolidone, a vinyl silane, a vinyl polyethylene oxide, a vinyl polypropylene oxide, or any combination thereof.

12. The coating composition of claim 1, further comprising an additional crosslinker, wherein the additional crosslinker is different from the crosslinker.

13. The coating composition of claim 12, wherein the additional crosslinker comprises a vinyl compound, an ethyleneglycol dimethacrylate, an acrylate compound, an epoxy compound, a urethane compound, an isocyanate compounds, a triacrylate, a methacrylate, a methacrylic acid, or a hydroxyethyl methacrylate.

14. The coating composition of claim 1, further comprising an additional crosslinker, wherein a ratio of the crosslinker to the additional crosslinker is between about 1:0.1 and about 1:10.

15. The coating composition of claim 14, wherein the ratio of the crosslinker to the additional crosslinker is between about 1:0.1 and about 1:1.

16. The coating composition of claim 1, further comprising an additive, wherein the additive is exposed at an outer surface of the coating or an exterior surface of the substrate.

17. The coating composition of claim 1, wherein the solvent comprises isopropanol, polypropanol, propanol, ethanol, methanol, dimethyl sulfoxide, water, or any combination thereof.

18. The coating composition of claim 1, wherein the high molecular weight component comprises polyethylene oxide, polypropylene oxide, polyvinylpyrrolidone (PVP), polyvinyl alcohol, a polyacrylate, an agarose, a methylcellulose, hyaluronan, polyisocynade, polyethylene oxide, alginate, carboxymethyl cellulose, a urethane coating, a water miscible epoxide, or any combination thereof.

19. The coating composition of claim 1, wherein the crosslinker induces a variable concentration of at least one hydrophilic component of the coating composition between the coating adjacent to an exterior surface of the substrate and an outer surface of the coating resulting in a variable hydrophilic nature of the coating providing greater water absorption near the outer surface of the coating relative to the coating adjacent to an exterior surface of the substrate.

20. A polymerizable coating composition, comprising:
an initiator;
a crosslinker configured to form a crosslinked polymer;
a high molecular weight component, wherein the high molecular weight component has an average molecular weight between about 30,000 and 1.5M; and
a solvent;
wherein polymerization of the composition on a substrate yields a coating comprising the high molecular weight component entrapped in the crosslinked polymer;
wherein the polymerizable coating composition is configured to covalently bond to the substrate, thereby forming a coating on the substrate.

* * * * *